(12) United States Patent
Sakata et al.

(10) Patent No.: US 7,879,057 B2
(45) Date of Patent: Feb. 1, 2011

(54) METHOD OF SETTING LANCING MEMBER TO LANCING DEVICE, LANCING DEVICE AND CAM MECHANISM

(75) Inventors: Tetsuya Sakata, Kyoto (JP); Daisuke Matsumoto, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 1327 days.

(21) Appl. No.: 10/519,881

(22) PCT Filed: Jul. 1, 2003

(86) PCT No.: PCT/JP03/08384

§ 371 (c)(1),
(2), (4) Date: Dec. 30, 2004

(87) PCT Pub. No.: WO2004/004566

PCT Pub. Date: Jan. 15, 2004

(65) Prior Publication Data

US 2005/0261716 A1    Nov. 24, 2005

(30) Foreign Application Priority Data

Jul. 2, 2002    (JP) .............................. 2002-193846

(51) Int. Cl.
*A61B 17/14*    (2006.01)
*A61B 17/32*    (2006.01)
*A61B 17/34*    (2006.01)
*A61B 5/00*    (2006.01)
*B65D 81/00*    (2006.01)

(52) U.S. Cl. ................ 606/182; 600/573; 600/583; 600/584; 606/181; 606/184; 606/185

(58) Field of Classification Search ......... 606/181–183, 606/184, 185; 600/583, 573, 584
See application file for complete search history.

(56) References Cited

U.S. PATENT DOCUMENTS

| 4,311,484 | A | * | 1/1982 | Fosslien ............... 73/864.21 |
| 5,314,442 | A | | 5/1994 | Morita |
| 5,454,828 | A | | 10/1995 | Schraga |
| 5,964,731 | A | * | 10/1999 | Kovelman .............. 604/110 |
| 5,989,917 | A | * | 11/1999 | McAleer et al. ............. 436/46 |

(Continued)

FOREIGN PATENT DOCUMENTS

EP    0 595 148    5/1994

(Continued)

OTHER PUBLICATIONS

Supplementary European Search Report from the corresponding EP 03 73 8627, mailed Dec. 20, 2007.

*Primary Examiner*—Max Hindenburg
*Assistant Examiner*—Sean P Dougherty
(74) *Attorney, Agent, or Firm*—Hamre, Schumann, Mueller & Larson, P.C.

(57) ABSTRACT

A lancing member (2) is integrally provided with a cap (29) for covering a needle (21). Upon or after being attached to a holder (5) of a lancing device (A), the lancing member (2) is rotated relative to a cap (29) by a rotator (C). As a result, the boundary (28) between the cap (29) and the lancing member (2) is broken easily to expose the needle (21).

7 Claims, 16 Drawing Sheets

U.S. PATENT DOCUMENTS

| | | |
|---|---|---|
| 6,315,738 B1 | 11/2001 | Nishikawa et al. |
| 6,352,514 B1 | 3/2002 | Douglas et al. |
| 7,001,364 B1 * | 2/2006 | Farhi .......................... 604/198 |
| 7,238,192 B2 | 7/2007 | List et al. |
| 7,500,967 B2 * | 3/2009 | Thorley et al. .............. 604/218 |

FOREIGN PATENT DOCUMENTS

| | | |
|---|---|---|
| EP | 1 238 632 | 9/2002 |
| JP | 05-285127 | 11/1993 |
| JP | 6-38909 | 5/1994 |
| JP | 6-133955 | 5/1994 |
| JP | 08-084721 | 4/1996 |
| JP | 2000-217804 | 8/2000 |
| JP | 2000-511068 | 8/2000 |
| JP | 2000-254111 | 9/2000 |
| JP | 2003-325484 | 11/2003 |
| WO | WO 93/19671 | 10/1993 |
| WO | 01/41643 | 6/2001 |

* cited by examiner

METHOD OF SETTING LANCING MEMBER TO LANCING DEVICE, LANCING DEVICE AND CAM MECHANISM

TECHNICAL FIELD

The present invention relates to a technique for simply and properly setting lancing member to a lancing device to sample body fluid such as blood.

BACKGROUND ART

Lancing devices are used by diabetics for sampling blood to measure the blood-sugar level. Such a lancing device generally comprises a cylindrical housing and a lancet holder reciprocally movable in the housing. A lancet is held in the lancet holder, and then the front end of the housing is pressed onto the skin. Thereafter, the lancet holder is advanced to pierce the skin by the needle of the lancet. In this way, the skin bleeds and blood can be sampled.

A conventional lancet, disclosed in JP-A-H6-133955, is shown in FIG. 18A. The illustrated lancet 9 includes a metal needle 91 which is supported by a body 90 made of synthetic resin. The body 90 is integrally formed by resin molding with a cap 92 for covering a tip end of the needle 91. The boundary 93 between the cap 92 and the body 90 is a narrow portion.

The needle 91 of the lancet 9 is covered by the cap 92, so that the needle 91 unused is kept clean. The cap 92 is twisted to break the boundary 93 to detach the cap 92 and the body 90, as shown in FIG. 18B, thereby exposing the tip end of the needle 91.

However, in the prior art, the setting of the lancet 9 to the lancing device is performed after the cap 92 is detached from the lancet 9, in a manner such that the separated lancet 9 is attached to a lancet holder of the lancing device. In this way, unfavorably, the exposed needle 91 of the lancet 9 may prick a finger of the user during the setting operation.

A solution to this problem may be detaching the cap 92 from the lancet 9 after the lancet 9 is attached to the lancet holder of the lancing device. However, even in this manner, the user still needs to pinch the cap 92 and twist it for breaking the boundary 93. Unfavorably, this task is troublesome. Moreover, a typical lancet-setting operation with respect to a lancing device may entail appropriate pushing of the lancet or lancet holder into the housing of the lancing device. In such a case, the setting of the lancet 9 can be more troublesome.

DISCLOSURE OF THE INVENTION

An object of the present invention is to provide a method of setting lancing member in lancing device as well as a lancing device for solving or alleviating the above problem. Further, another object of the present invention is to provide a cam mechanism for being used in such lancing device.

According to a first aspect of the present invention, there is provided a method of setting lancing member in lancing device. The method comprises: a first step for causing a lancing member formed integral with a cap covering a needle to be held by a holder of a lancing device; and a second step for breaking a boundary between the cap and the lancing member by rotating the lancing member relative to the cap utilizing rotating means prearranged at the lancing device. The second step is performed during or after the first step. Preferably, the method of the present invention further comprises a third step for exposing the needle by detaching the cap from the lancing member after the second step.

Preferably, the lancing device comprises a housing including a tip end formed with an opening, and the holder is reciprocally movable in the housing. The rotating means comprises a cam mechanism for rotating the holder and the lancing member utilizing a pressing force exerted when the holder is pressed into the housing by the lancing member.

Preferably, the lancing member is held by a supporting member including a sheath. In the first step, the sheath is slidably fitted to an end of the housing. The lancing member is pressed against the holder to be pushed into the housing. The sheath may be generally circular or generally polygonal.

Preferably, the supporting member may hold an analyzer. In the first step, the analyzer is attached to the lancing device when the lancing member is held by the holder.

Preferably, the rotating means may comprise a motor. In the second step, the lancing member is rotated by driving force of the motor.

According to a second aspect of the present invention, there is provided a lancing device comprising: a holder for holding a lancing member; a moving mechanism for advancing the holder in a predetermined direction; and rotating means for rotating the lancing member when the lancing member is about to be held by the holder or after the lancing member is held by the holder.

Preferably, the holder may hold the lancing member in a manner such that the holder and the lancing member are not rotatable relative to each other. The rotating means rotates the holder together with the lancing member.

Preferably, the rotating means may comprise a cam mechanism for rotating the holder when the holder retracts in a direction opposite to the predetermined direction.

Preferably the lancing device may further comprise a cylindrical housing that contains the holder therein and includes a tip end formed with an opening. The cam mechanism includes a first groove which is provided at one of the housing and the holder and is inclined relative to a longitudinal axis of the housing, and also includes a protrusion which is provided at the other one of the housing and the holder and is fitted in the first groove.

Preferably, the cam mechanism may further include a second groove connected to the first groove and extending in parallel to the axis of the housing. The protrusion passes through the second groove when the holder advances.

Preferably, the rotating means may comprise a motor and a member for transmitting rotating force of the motor to the holder.

Preferably, the lancing device may further comprise a holding portion for removably holding an analyzer used for analyzing a sample taken by piercing process.

Preferably, the lancing device may further comprise a control circuit for analyzing the sample using the analyzer.

According to a third aspect of the present invention, there is provided a cam mechanism comprising: a cylindrical housing; a movable member contained in the housing for moving reciprocally in first and second directions parallel to a longitudinal axis of the housing; a first groove inclined relative to the axis of the housing and a second groove connected to the first groove and extending linearly in parallel to the axis of the housing, the first and the second grooves being provided at one of the housing and the movable member; and a protrusion provided at the other one of the housing and the movable member, the protrusion extending into the first groove and the second groove. The protrusion moves in the first groove when the movable member moves in the first direction, while moves in the second groove when the movable member moves in the second direction.

Other features and advantages of the present invention will be apparent from the following description of the embodiments according to the present invention.

BRIEF DESCRIPTION OF THE DRAWINGS

FIG. 3A is a perspective view illustrating an example of a capped lancet held in the lancing unit shown in FIG. 1, while

FIG. 5A is a perspective view illustrating an example of a sensor attached to the sensor holder shown in FIG. 4, while

BEST MODE FOR CARRYING OUT THE INVENTION

Preferred embodiments according to the present invention will be described below with reference to the drawings.

FIGS. 1-6 illustrate an example of a lancing unit used for a method of setting a lancing member in a lancing device according to the present invention. For facilitating the understanding of the present invention, the illustrated lancing unit U is described first.

Figure 1:
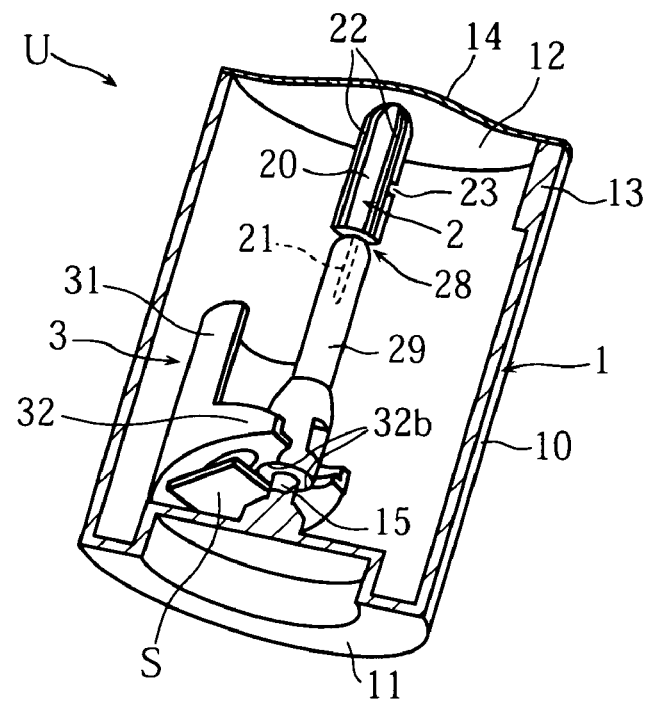
FIG. 1 is a perspective view illustrating an example of a lancing unit, with some part removed, used for a lancing member setting method according to the present invention.
Figure 2:
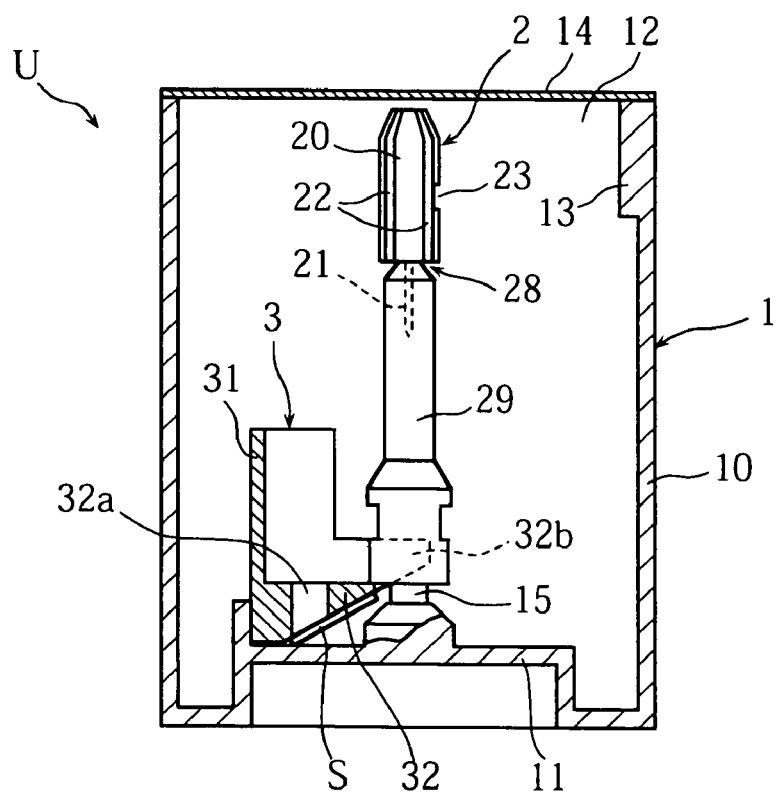
FIG. 2 is a sectional side view showing the unit of FIG. 1.

As shown in FIG. 1 and FIG. 2, the lancing unit U includes a case 1, a lancet 2, a cap 29, and a sensor holder 3.

The case 1, in the form of a cap made of e.g. synthetic resin, includes a cylindrical sheath 10, which is formed with an opening 12 at one end (upper end), and also includes a bottom 11 which is formed integral with the sheath 10 at the other end (lower end). The case 1 is an example of a 'supporting member including a sheath' according to the present invention. As will be described later, the case 1 is externally fixed to a predetermined portion of a lancing device A, and the sheath 10 is internally formed with a stopper 13 for preventing rotation of the case 1 in the lancing device. The opening 12 of the case 1 is closed by a film 14 serving as a lid attached to the top of the case, so that the case 1 is hermetically sealed. The film 14 is made of aluminum foil or laminated film of aluminum foil and resin film, for example.

Figure 3A:
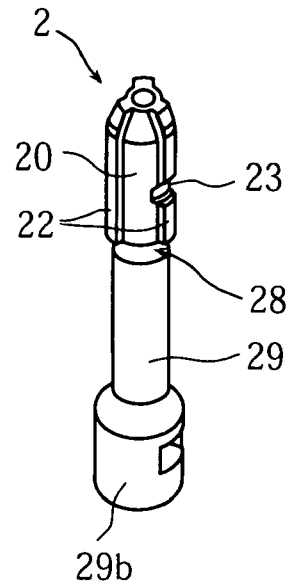
Figure 3B:
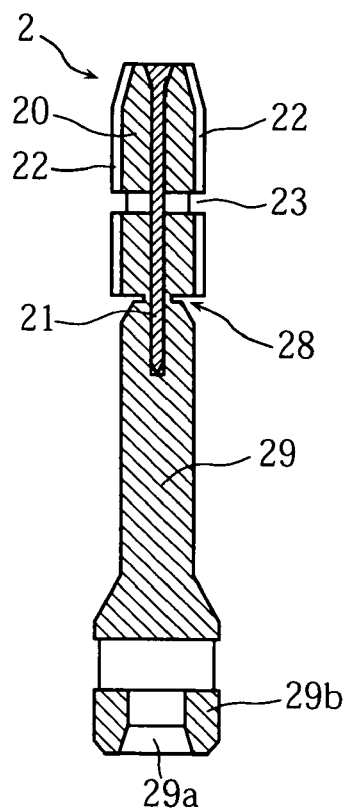
FIG. 3B is a sectional view of the lancet.

As shown in FIGS. 3A-3B, the lancet 2 includes a metal needle 21 and a synthetic resin body 20 for holding the needle 21. The body 20 is formed with a plurality of ribs 22 extending in parallel to the needle 21, and with a groove 23, so that it can be properly attached to a lancet holder 5 of the lancing device A, as will be described later.

Figure 6:
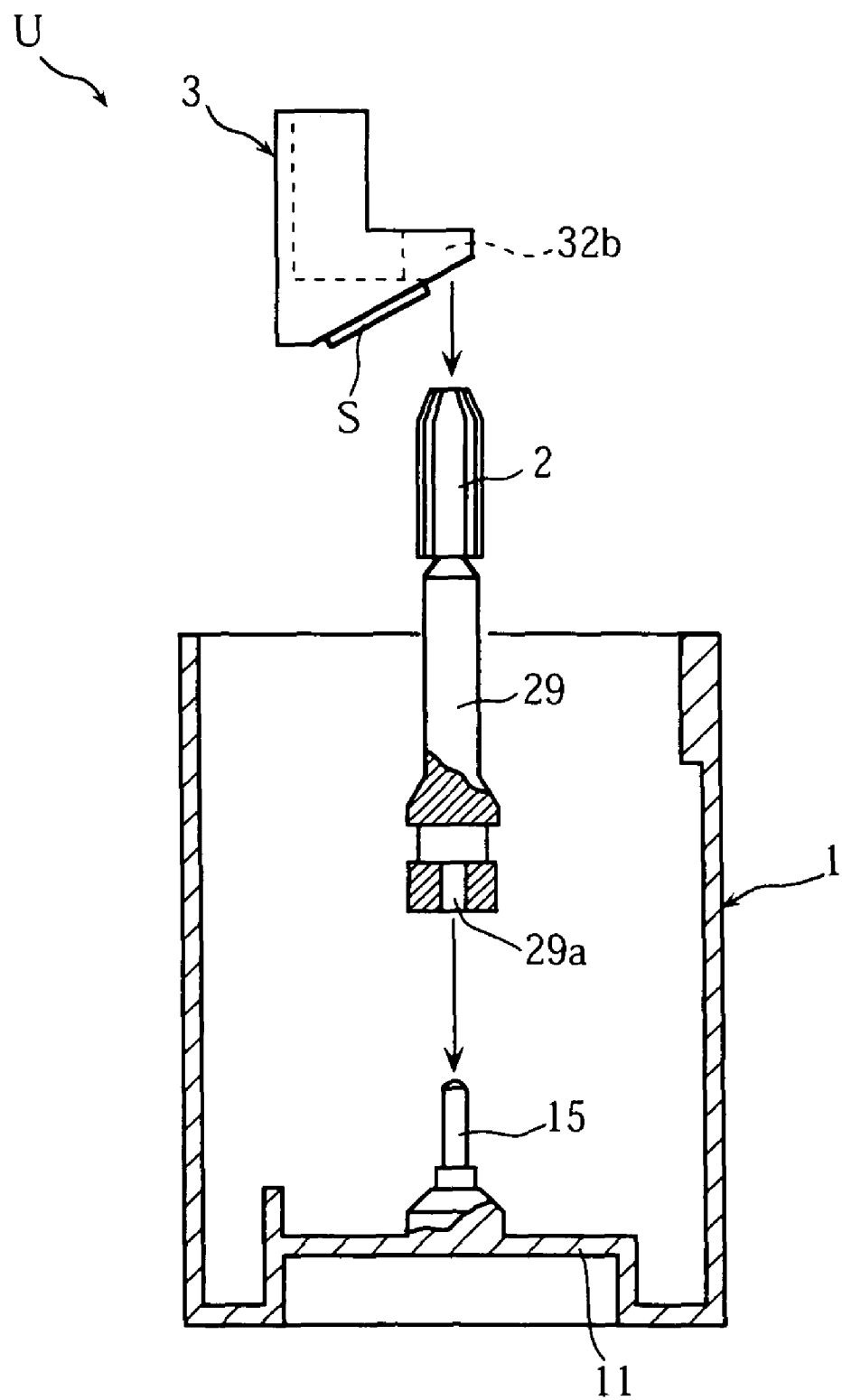
FIG. 6 is an exploded view, partly in section, showing the lancing unit of FIG. 1.

The cap 29, formed by resin molding, is integral with the body 20 to cover the tip end of the needle 21 protruding from the body 20, and extends in the longitudinal direction of the needle 21 below the tip end (bottom end) of the body 20. The boundary 28 between the cap 29 and the body 20 is formed narrower than the other portions to facilitate the detaching the cap and the body. As shown in FIG. 6, the cap 29 includes a bottom end formed with a hole 29a into which a protrusion 15 formed on the bottom 11 of the case 1 is fitted. Thus, the cap 29 is held vertically in the case 1. Contrary to the above structure, the case 1 may have a recess formed at the bottom 11, while the cap 29 may have a protrusion formed at its bottom to be fitted into the recess. The cap 29 is fixed to the case 1 by an adhesive for reliable attachment to the case 1. For this fixation, the adhesive may be replaced with ultrasonic welding or heat welding, for example. This may also apply to attachment of other parts of the lancing unit. The needle 21 of the lancet 2 is sterilized by e.g. gamma irradiation before being arranged in the case 1. Preferably, the case 1 is provided with a drying agent (not shown) for quality protection of a sensor S which will be described later. According to the present invention, the cap 29 and the body 20 may be integrally formed with the case 1, in place of being formed separately.

Figure 4:
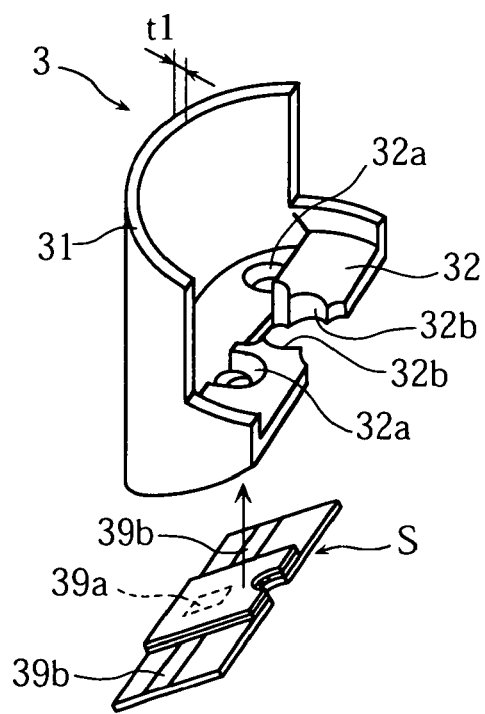
FIG. 4 is a perspective view illustrating an example of a sensor holder held in the lancing unit shown in FIG. 1.

The sensor holder 3 holds a sensor S used for blood analysis. The sensor holder 3 is made of synthetic resin, and as shown in FIG. 4, includes a side wall 31 which is arcuate in section and a horizontal wall 32 which is integrally formed with the side wall 31. The horizontal wall 32 includes an inclined underside to which the sensor S is attached.

Figure 5A:
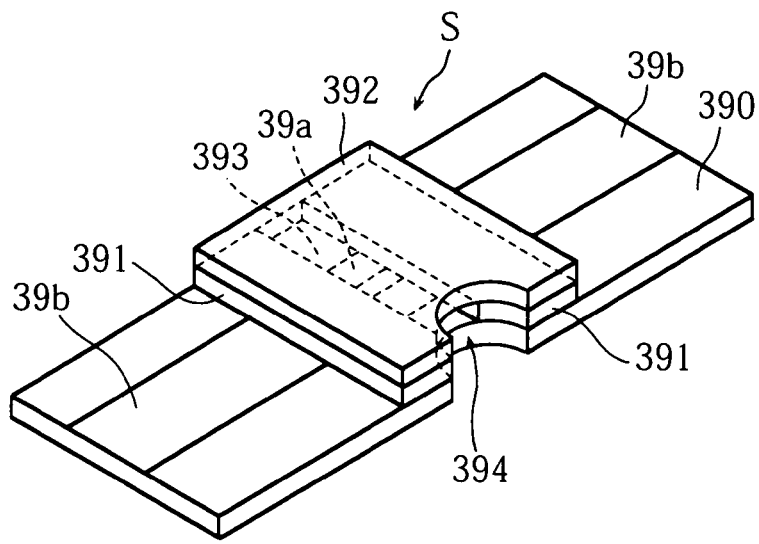
Figure 5B:
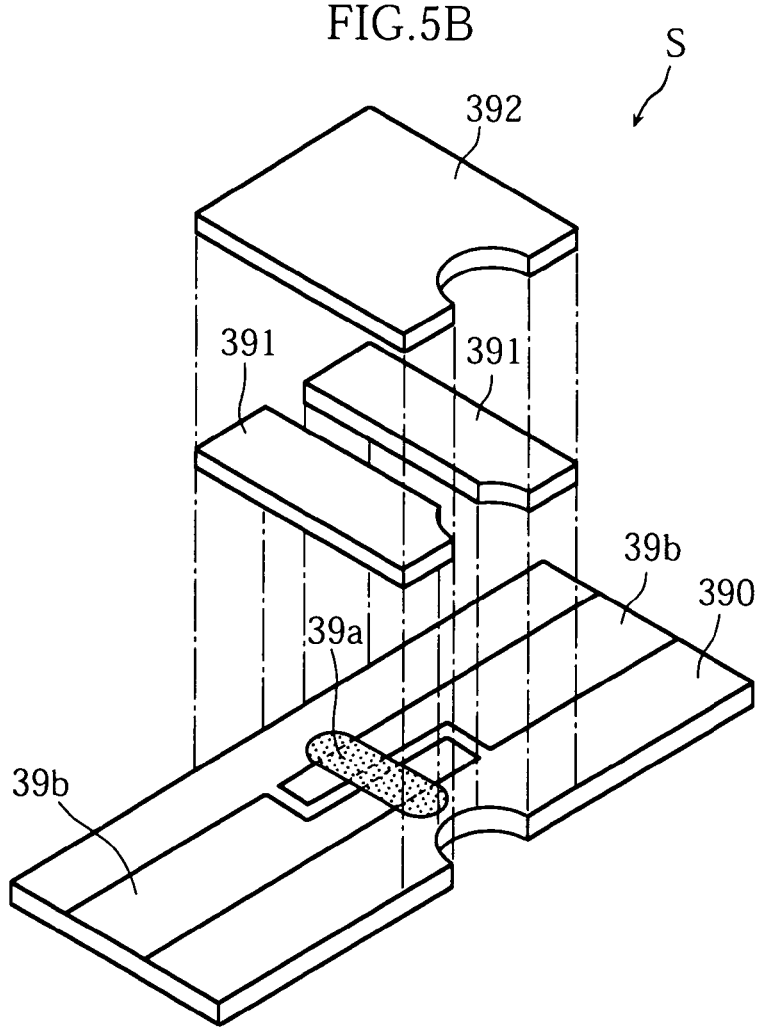
FIG. 5B is an exploded perspective view of the sensor.

The sensor S is in the form of a chip and may have a structure shown in FIGS. 5A-5B. Specifically the sensor S includes a base plate 390 having an upper surface provided with a reagent 39a and a pair of electrodes 39b, where the reagent contains an enzyme reactive to the glucose in blood in a certain way (e.g. oxidation), and the electrodes electrically detect the reaction. On the base plate 390, a capillary 393 is formed by two separate spacers 391 and a cover 392 which is stacked on the spacers 391. The assembly of the base plate 390, spacers 391 and cover 392 is formed with a recess 394 as an inlet of blood. When supplied to the recess 394, the blood flows through the capillary 393 by capillary action, to be led to the reagent 39a.

As shown in FIG. 4, the horizontal wall 32 of the sensor holder 3 is formed with a pair of through-holes 32a and a pair of supporting wall portions 32b. The through-holes 32a permit insertion of a pair of probes 62 of a lancing device A, so that the probes 62 come into contact with the electrodes 39b of the sensor S. The supporting portions 32b can be externally pressed onto the bottom portion 29b of the cap 29 in a sandwiching manner. The bottom portion 29b of the cap 29 may be cylindrical, while the supporting wall portions 32b are substantially arcuate correspondingly to the outer circumference of the cap's bottom portion. As shown in FIGS. 1 and 2, since the wall portions 32b are externally fixed to the bottom portion of the cap 29, the sensor holder 3 is supported by the case 1 via the cap 29. It should be noted here that the sensor holder 3 is slidable relative to the cap 29 in the longitudinal direction of the cap 29, and further, as described below, the sensor holder can be detached from the cap 29.

As the lancing unit U is sealed by the film 14, the reagent 39a of the sensor S is kept free from moisture, thereby preventing quality deterioration in the short term. Further, the needle 21 of the lancet 2 is covered by the cap 29, and the cap 29 is integrally formed with the body 20 of the lancet 2. Due to such highly hermetical sealing, the lancet 2 is kept free from contamination even before the lancet 2 is set in the case 1.

To assemble the lancing unit U, the lancet 2 integral with the cap 29 is set in the case 1, and then the sensor holder 3 is attached to the cap 29. Next, the film 14 is provided to cover the opening 12 of the case 1. The setting of the lancet 2 is performed by fixing the protrusion 15 of the case 1 into the hole 29a of the cap 29, the setting of the sensor holder 3 is performed by externally fitting the supporting portions 32b to the cap 29. In this manner, it is easy to assemble the lancing unit U, whereby the production costs are lowered.

Figure 7:
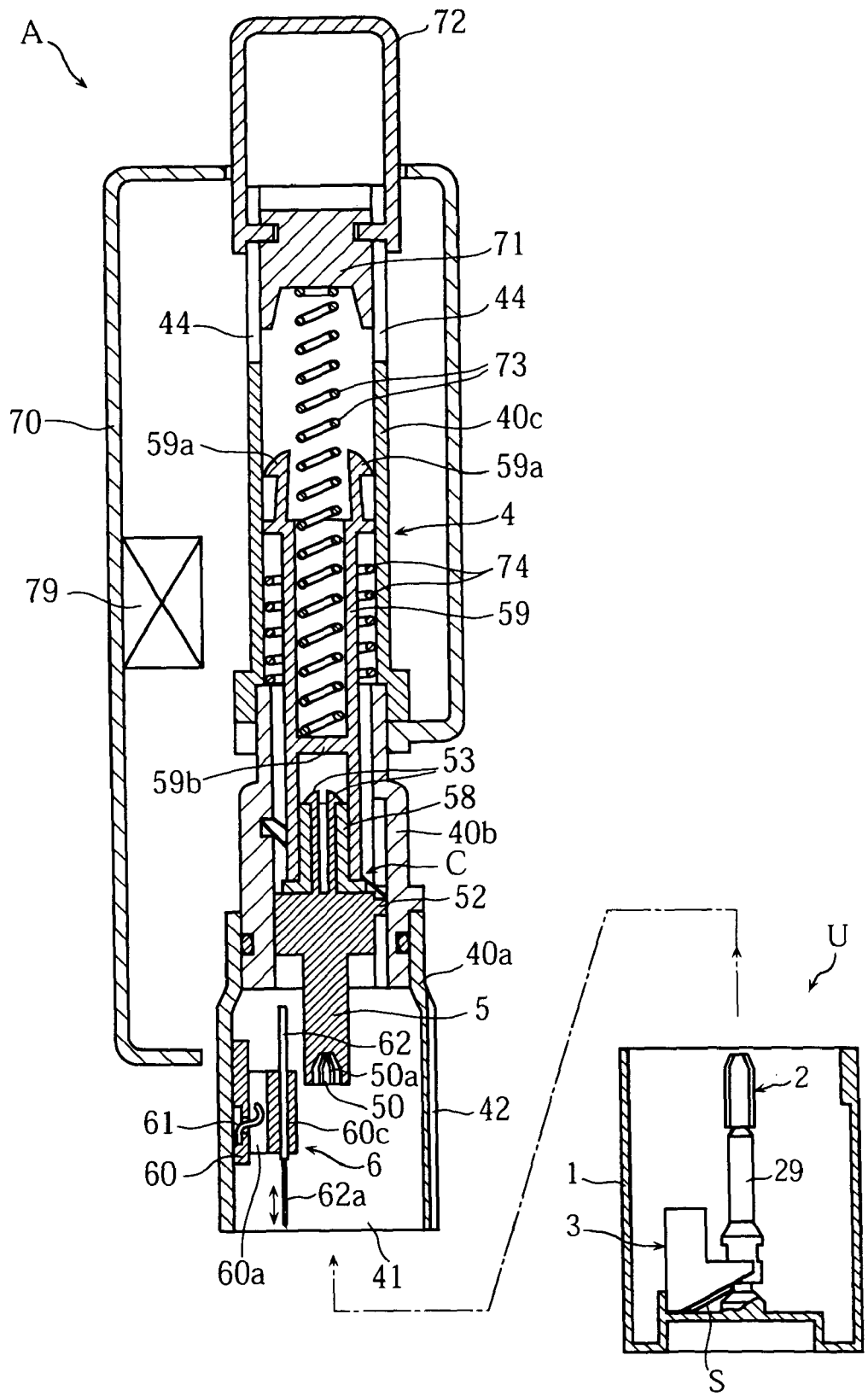
FIG. 7 is a sectional view illustrating an example of a lancing device according to the present invention.
Figure 8:
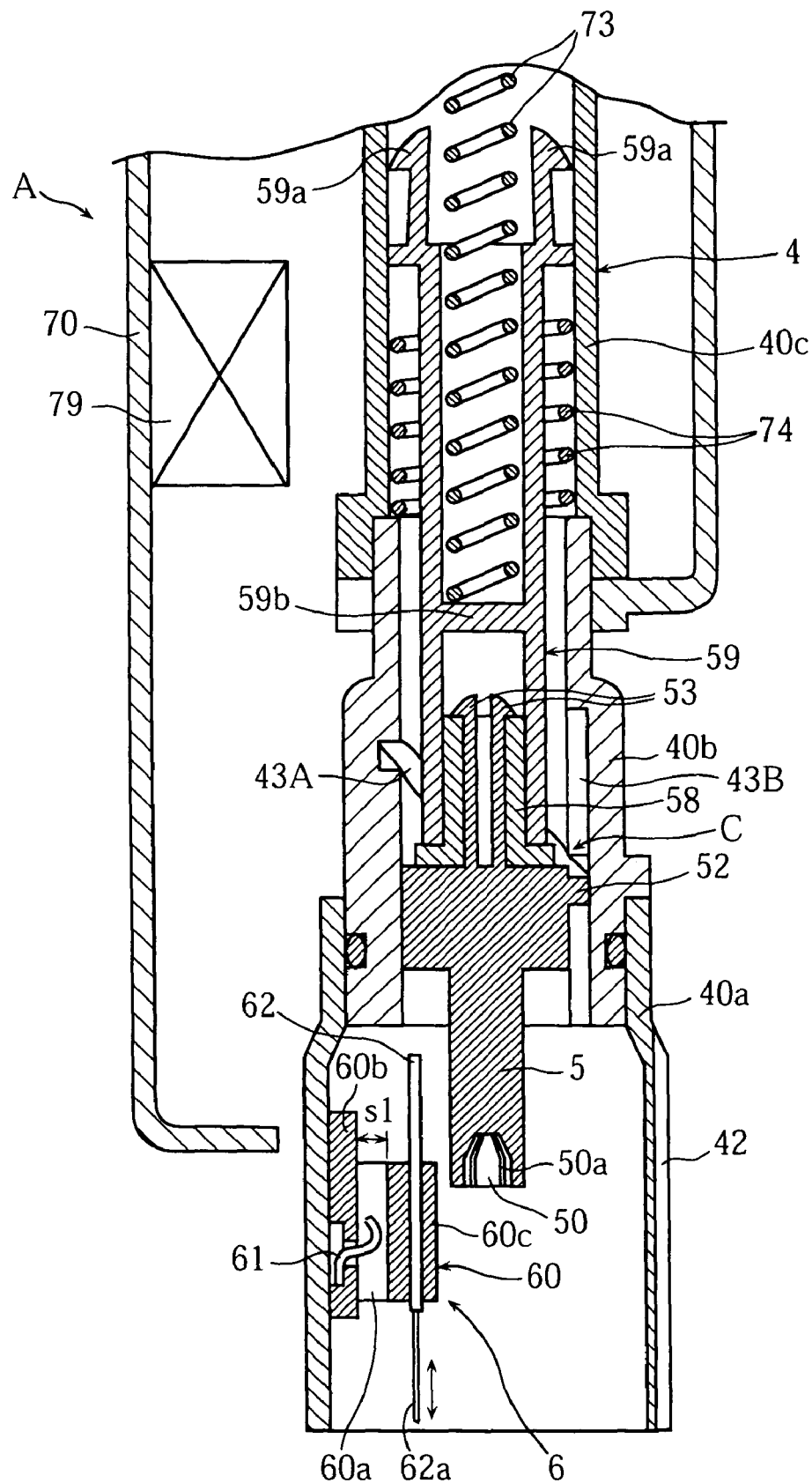
FIG. 8 is an enlarged sectional view of a principal part of the device shown in FIG. 7.

FIGS. 7 and 8 illustrate an example of a lancing device according to the present invention. As shown in FIG. 7, the lancing device A of the present embodiment includes a housing 4, a lancet holder 5, a latch 59, and a cam mechanism C.

Figure 11:
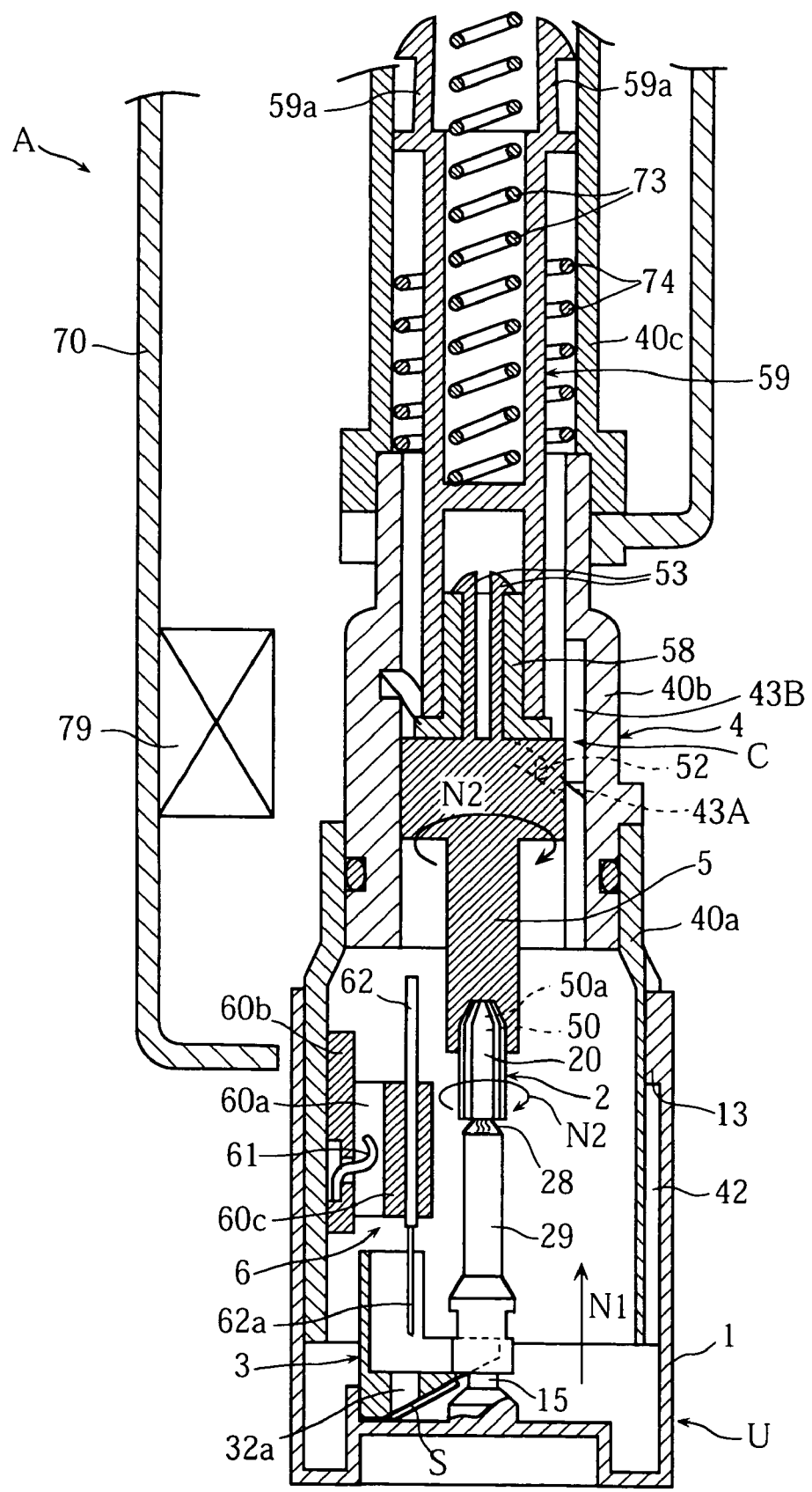
FIG. 11 is an enlarged sectional view illustrating an earlier stage of attaching the lancet and the sensor holder of the lancing unit to the lancing device shown in FIG. 7.

The housing 4 includes three sleeves 40a-40c which are serially connected to each other, each serving as a front portion, an intermediate portion, and a rear portion, the housing being held by an outer case 70. The tip end (bottom end) of the sleeve 40a, formed with an opening 41, is brought into contact with human skin. As shown in FIG. 11, the sleeve 40a is formed and sized to be slidably fitted with the case 1 of the lancing unit U. The sleeve 40a is externally formed with a groove 42 into which the stopper 13 of the case 1 is fitted. The groove 42 extends lengthwise of the sleeve 40a to prevent the case 1 from rotating when the case 1 is externally fitted to the sleeve 40a. When the lancet 2 and the sensor holder 3 of the lancing unit U are set to the lancing device A, the case 1 is brought into sliding engagement with the sleeve 40a, so that the lancet 2 and the sensor holder 3 are properly arranged at predetermined positions in the lancing device A as described later.

Figure 12:
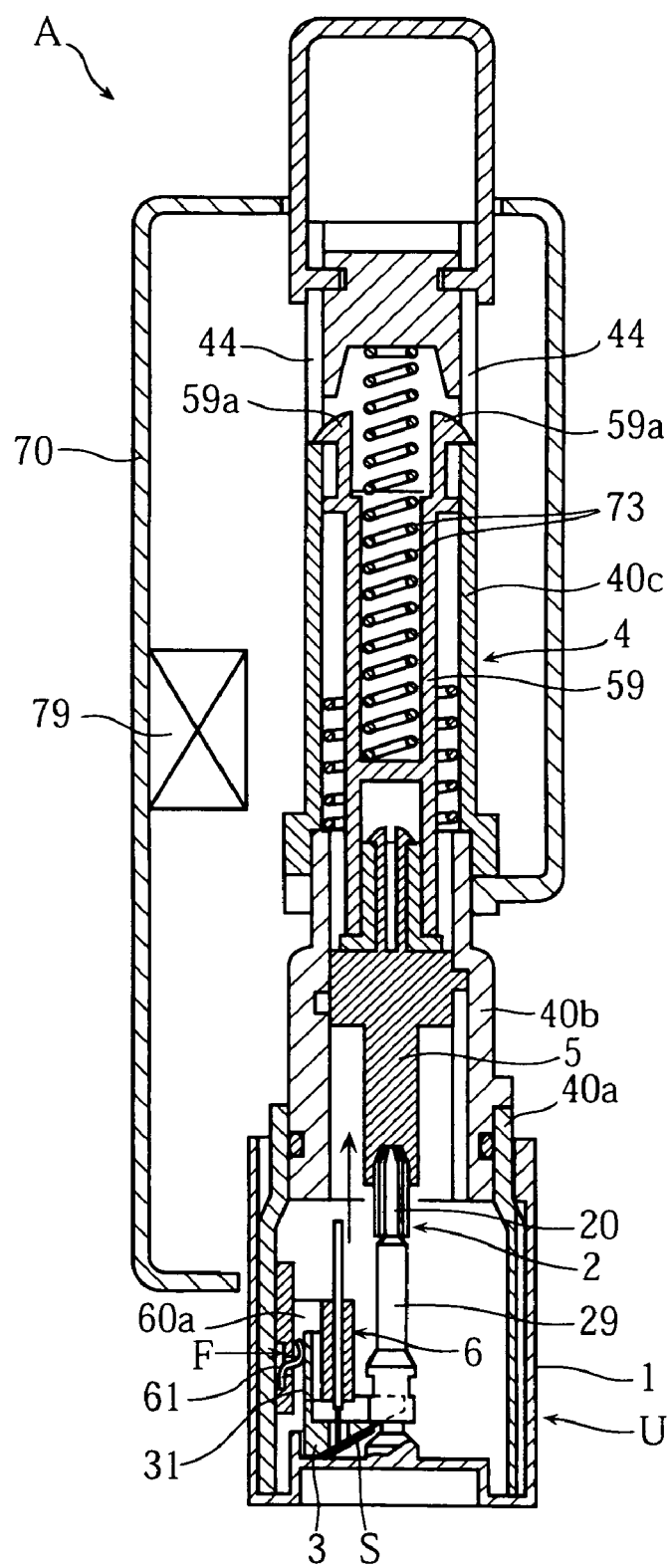
FIG. 12 is a sectional view illustrating an intermediate stage of attaching the lancet and the sensor holder of the lancing member to the lancing device shown in FIG. 7.
Figure 13:
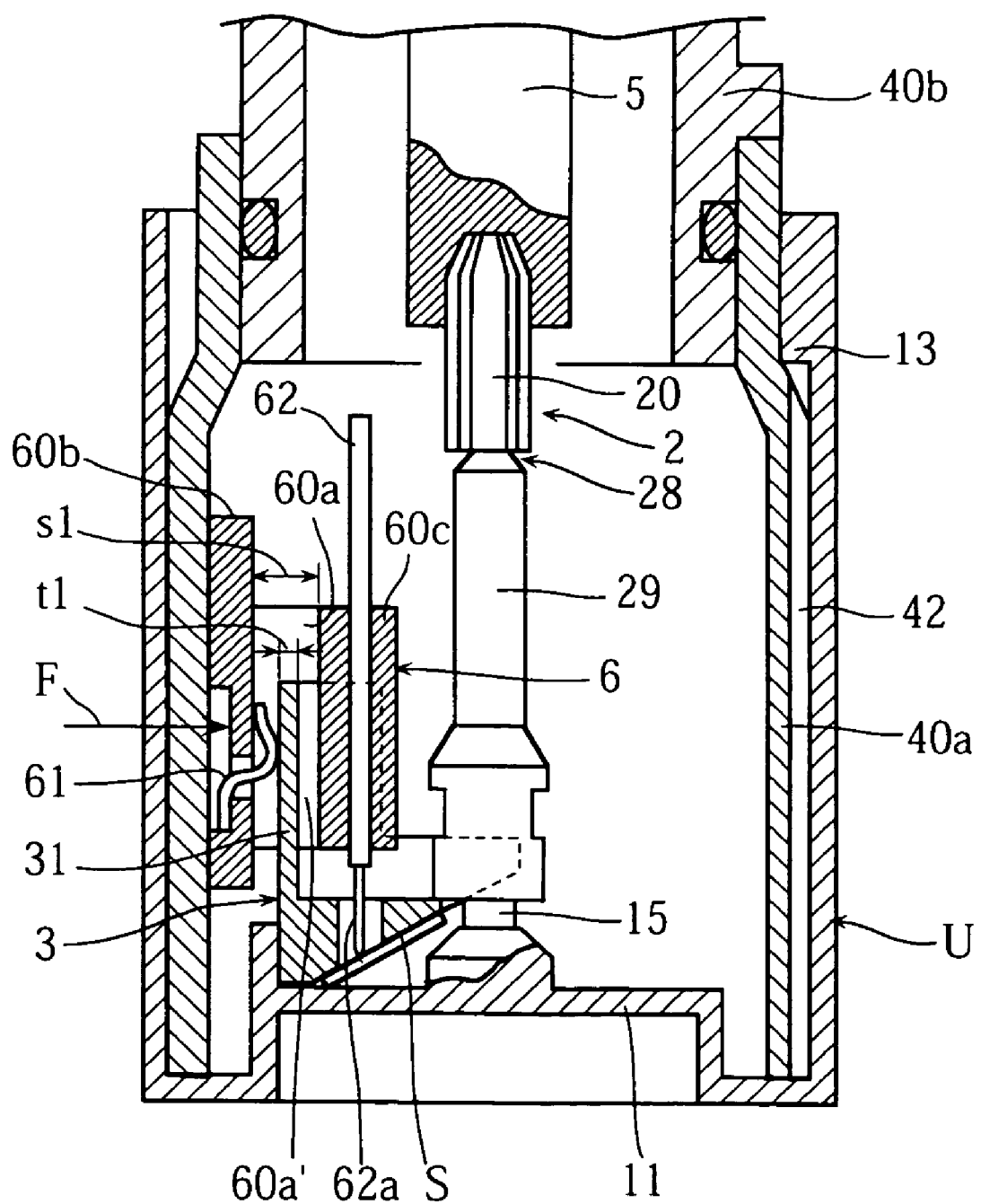
FIG. 13 is a sectional view showing a principal part of FIG. 12.
Figure 14:
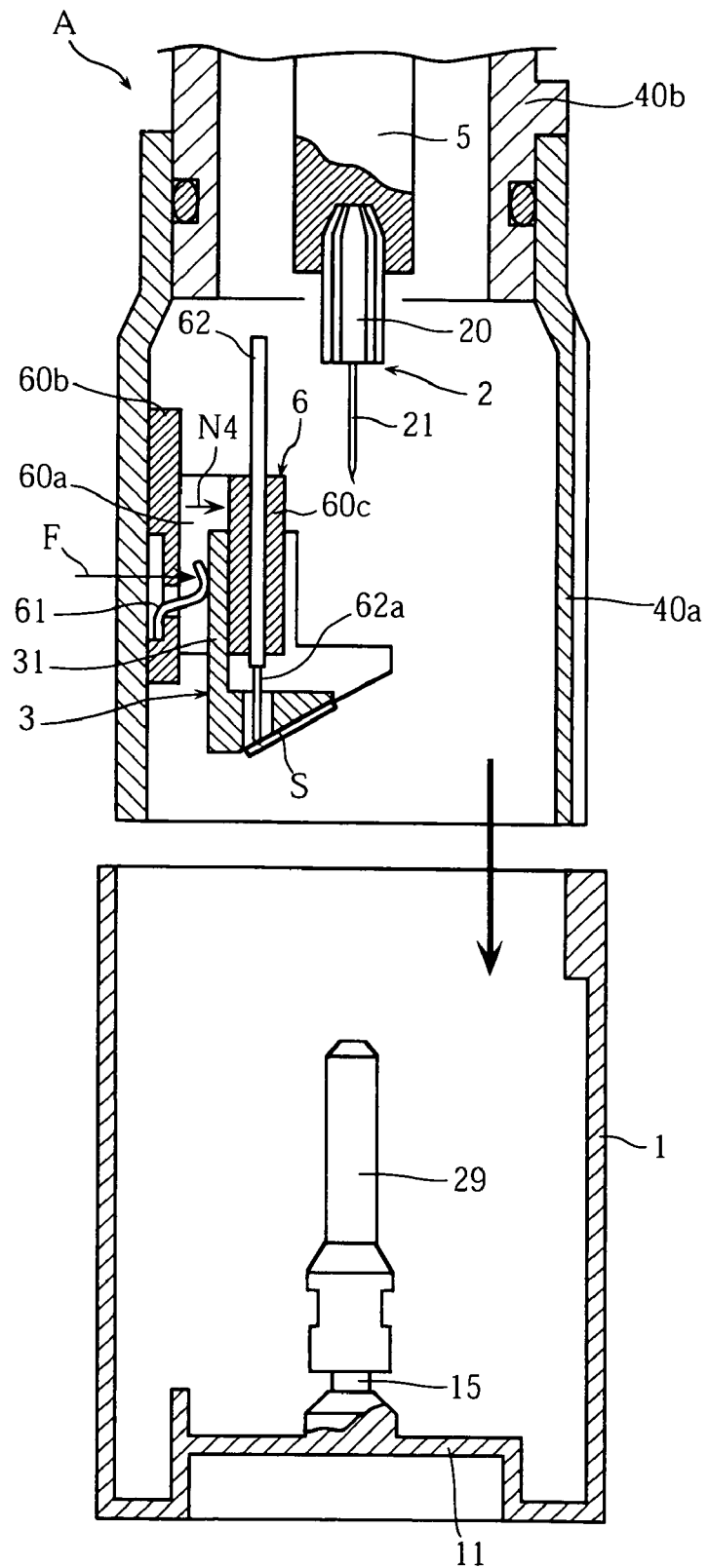
FIG. 14 is an enlarged sectional view illustrating a final stage where the fixing of the lancet and sensor holder of the lancing unit to the lancing device shown in FIG. 7 has been completed.

As shown in FIG. 8, the sleeve 40a is provided with a holding portion 6. The holding portion 6 serves to hold the sensor holder 3 of the lancing unit U and includes an attachment 60 fixed to the sleeve 40a. The attachment 60 is made of synthetic resin and includes a space 60a formed by first and second walls 60b, 60c. As shown in FIGS. 12 and 13, the space 60a permits the insertion, from its bottom side, of the side wall 31 of the sensor holder 3 of the lancing unit U. A width s1 of the space 60a is larger than the thickness t1 of the side wall 31 of the sensor holder 3. With such an arrangement, when the side wall 31 is inserted into the space 60a, with the sensor holder 3 set in the case 1, there is a space 60a' formed between the side wall 31 and the second wall 60c. The holding portion 6 is provided with a spring 61. When the side wall 31 is inserted into the space 60a, the spring 61 exerts urging force F which presses the side wall 31 toward the second wall 60c. Thus, as shown in FIG. 14, when the sensor holder 3 is released from the cap 29, the urging force F of the spring 61 presses the side wall 31 onto the second wall 60c, whereby the sensor holder 3 is held by the holding portion 6. For holding the sensor holder 3 more reliably, use may be made of appropriate engaging means which can come into releasable engagement with the sensor holder 3 and the holding portion 6.

In FIGS. 7 and 8, a pair of probes 62 is held by the second wall 60c of the holding portion 6. The probes 62, extending in the longitudinal direction of the housing 4, come into contact with the electrodes 39b of the sensor S. Each probe 62 includes a retractable tip end 62a. When the sensor holder 3 is not attached to the lancing device A, each tip end extends downwardly by urging force of a suitable spring (not shown). On the other hand, as shown in FIGS. 12-14, when the sensor holder 3 is attached to the holding portion 6, the tip end 62a is pressed upwardly by the sensor S and retracts. The outer case 70 is provided with a control circuit 79 electrically connected to the probes 62. The control circuit 79 includes a CPU and attached memory, for example, for calculating glucose level in blood introduced to the reagent 39a, based on an electric current measured by the probes 62.

The lancet holder 5 for holding and moving the lancet 2 is an example of a holder (for holding a lancing member). The lancet holder 5 is rotatably inserted in the sleeve 40b, while also being slidable in the longitudinal direction of the sleeve. The lancing holder 5 includes a bottom portion formed with a recess 50. The recess 50 permits the insertion of the body 20 of the lancet 2, so that the lancing holder 5 removably holds the lancet 2.

The recess 50 is internally formed with a plurality of grooves 50a in which the ribs 22 of the body 20 of the lancet 2 are fitted in. Due to this structure, the body 20 and the lancet holder 5 are prevented from rotating relatively when the body 20 is inserted in the recess 50. It should be noted that either of the grooves 50a and the ribs 22 is partially or wholly formed in spirals. Thus, when the body 20 of the lancet 2 is inserted in the recess 50, as will be described later, the body 20 and the lancet holder 5 rotate in a predetermined direction through a relatively small angle.

Figure 9:
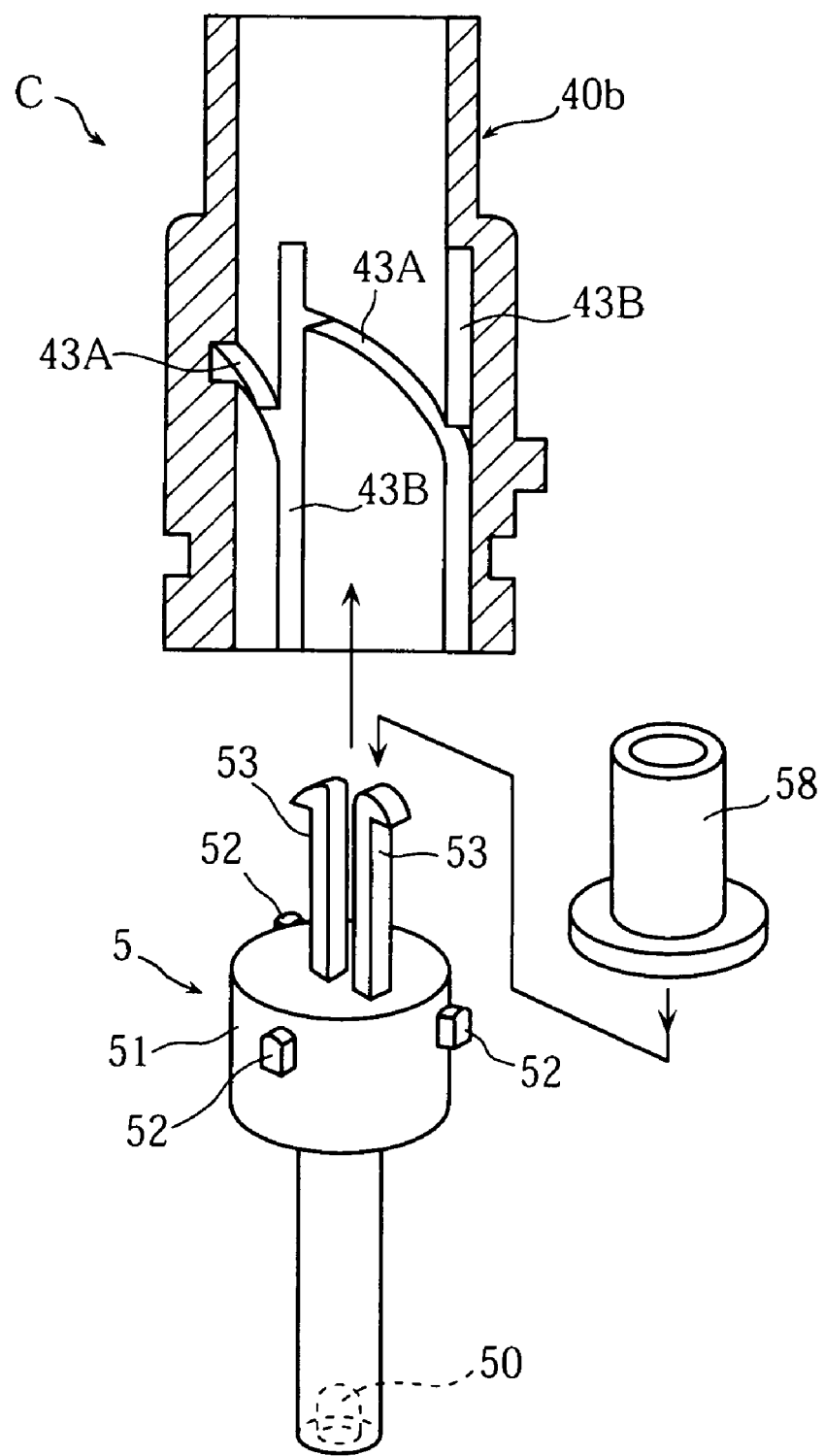
FIG. 9 illustrates an example of a cam mechanism provided in the lancing device shown in FIG. 7.

The cam mechanism C is made up of the lancet holder 5 and the housing 4. As shown in FIG. 9, the lancet holder 5 includes a head portion 51 which is circumferentially formed with a plurality of protrusions 52 at an equal angular spacing. The protrusions 52 are inserted into and guided by first grooves and second grooves 43A, 43B which are internally formed in the sleeve 40b of the housing 4. The lancet holder 5 is an example of a moving portion of a cam mechanism according to the present invention.

The first grooves 43A are inclined relative to the longitudinal axis of the sleeve 40b for rotating the lancet holder 5 when the lancet holder 5 is pushed upward by the lancet 2 of the lancing unit U. On the other hand, the second grooves 43B extend in parallel to the axis of the sleeve 40b for guiding the lancet 2 and the lancet holder 5 linearly toward the tip end of the housing 4 to pierce human skin by the lancet 2.

Figure 10A:
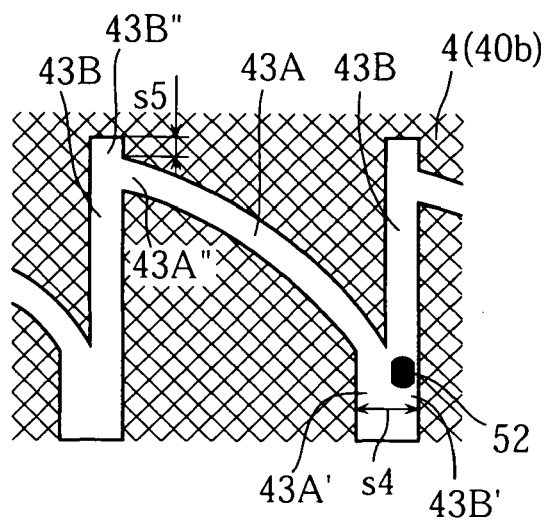
FIGS. 10A-10E illustrate the workings of the cam mechanism shown in FIG. 9.
Figure 10B:
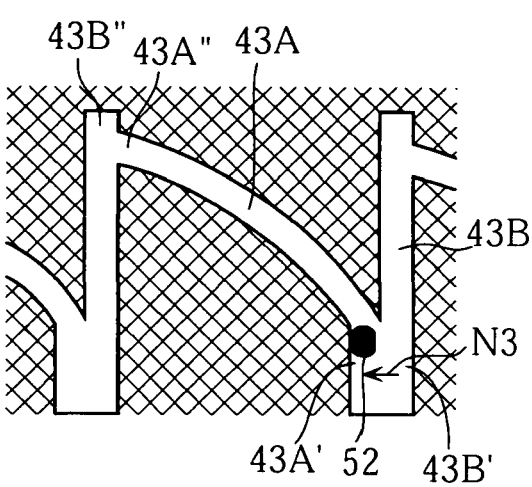

FIGS. 10A-10E show part of the first and the second grooves 43A, 43B expanded in a plane, where these grooves are connected to each other (in the figures, areas other than the first and second grooves 43A, 43B are indicated by hatching). As shown in FIG. 10A, the first and second grooves include ends (bottom ends) 43A', 43B' which are arranged circumferentially of the housing 4 and connected to each other so that the total width s4 is relatively large. On the other hand, the other ends (top ends) 43A", 43B" of the first and the second grooves are connected to each other in a manner such that the end 43B" projects beyond the end 43A" by an appropriate distance s5. When the lancet holder 5 is moved in the longitudinal direction of the housing 4, the protrusions 52 are guided along the first and second grooves 43A, 43B. The movement will be specifically described later.

As shown in FIGS. 7 and 8, the latch 59 is connected to the top of the lancet holder 5, and slidably inserted in the housing 4. A bushing 58 is non-rotatably fitted into the bottom of the latch 59A. The top of the lancet holder 5A is formed with a plurality of claws 53 to be rotatably inserted in the bushing 58. With such arrangements, the lancet holder 5 is rotatable, whereas the latch 59 does not rotate together with the lancet holder. The top of each claw 53 comes into non-extractable engagement with the top of the bushing 58 for connection of the lancet holder 5 and the latch 59.

Figure 16:
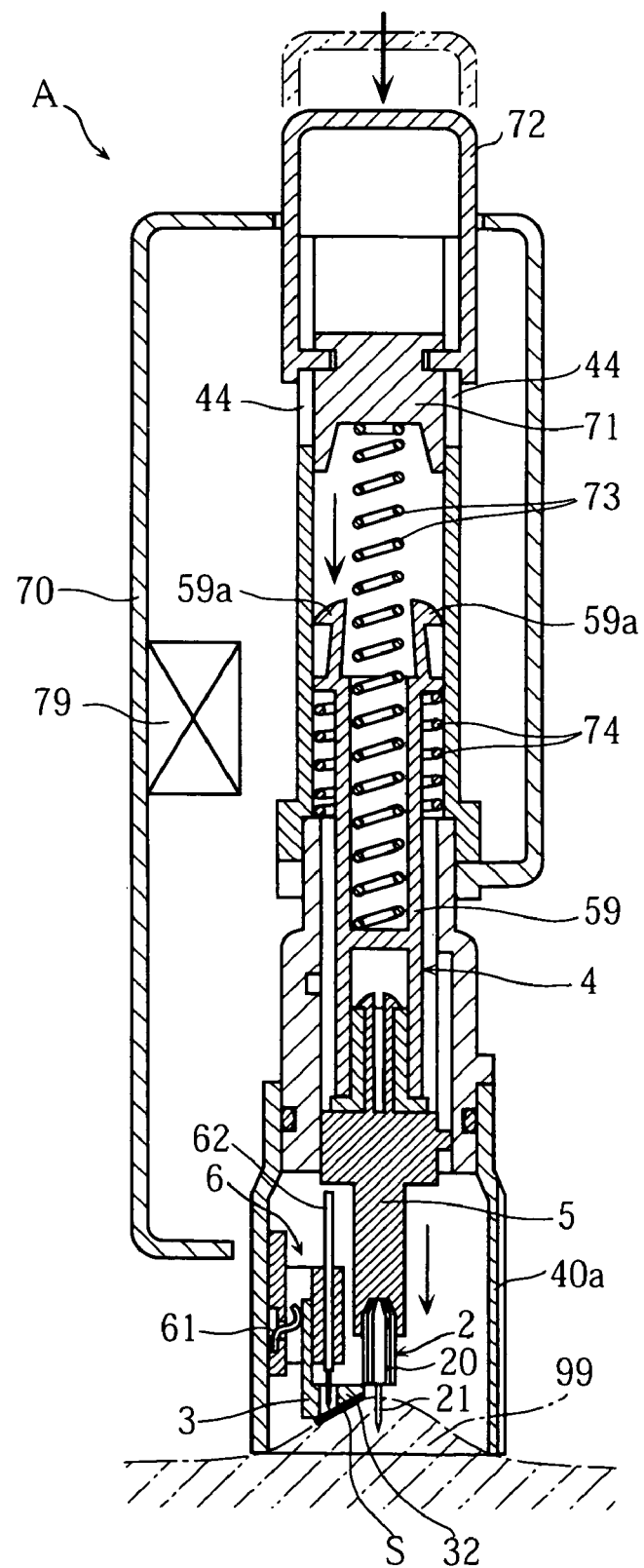
FIG. 16 is a sectional view illustrating how to use the lancing device shown in FIG. 7.

The latch 59 is formed with a pair of claws 59a at the top. Each of the claws 59a comes into engagement with an end of one of the cutouts 44 formed at the sleeve 40c. As will be described below, the engagement is established when the lancet holder 5 and the latch 59 are pressed upwardly by the lancet 2 of the lancing unit U. The sleeve 40 is provided, at the top, with a latch-releasing pusher 71 and an operating cap 72 connected to the pusher. A spring 73 is provided between the pusher 71 and an intermediate wall 59b of the latch 59. The spring 73 is a compressed coil spring, for example. The operating cap 72 is slidable relative to the sleeve 40c in the longitudinal direction of the sleeve. When the cap 72 is pressed downward against the spring 73, the pusher 71 moves downward to press the latch claws 59a. In this way, as shown in FIG. 16, the claws 59a are forcibly disengaged from the ends of the cutouts 44, whereby the latch 59 and the lancet holder 5 are advanced downward due to the restoring force of the compressed spring 73. The housing 4 is internally provided with a return spring 74 for moving the lance holder 5 and the latch 59 back after they have advanced.

A method of setting the lancet 2 to the lancing device A and the workings of the lancing device A are now described below.

First, as shown in FIG. 11, the case 1 of the lancing unit U is externally fitted to the sleeve 40a of the lancing device A. Before this step, the film 14 is removed from the case 1 to open the opening 12. When the case 1 is externally fitted to the sleeve 40a, the body 20 of the lancet 2 is fitted into the recess 50 of the lancet holder 5 to be held at the lancet holder 5. Then the case 1 is pressed upwardly in the direction of a narrow N1, whereby the lancet holder 5 is pressed upwardly by the lancet 2. In this step, the lancet holder 5 and the body 20 of the lancet 2 rotate in the direction of an arrow N2, until the boundary 28 of the lancet 2 and the cap 20 is twisted to be broken.

More specifically, as shown in FIG. 10A, the protrusions 52 of the lancet holder 5 are initially placed within the end 43B' of the second groove 43B. When the lancet 2 is fitted into the recess 50, each protrusion 52 is moved to the end 43A' of the groove 43A, as indicated by an arrow N3 in FIG. 10B. This movement is caused by the rotation of the lancet holder 5 when the body 20 is fitted in the recess 50, because of the spiral form of either the ribs 22 in the body 20 of the lancet 2 or the grooves 50a in the recess 50 of the lancet holder 5.

Figure 10C:
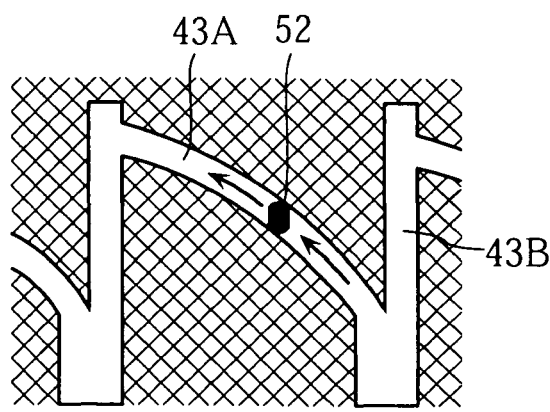
Figure 10D:
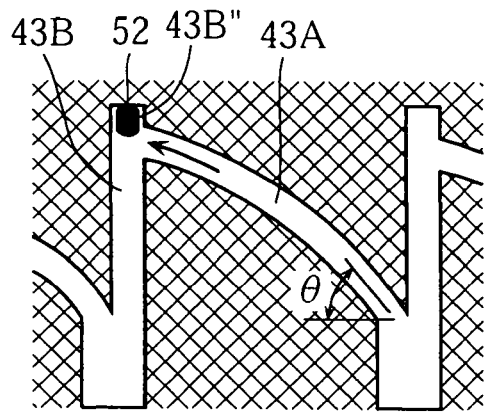

While the lancet holder 5 is being pressed upwardly by the lancet 2, the protrusions 52 move within the first grooves 43A, as shown in FIGS. 10C and 10D. Due to this movement, the lancet holder 5 rotates together with the body 20 of the lancet 2. On the other hand, the cap 20 of the lancing unit U is fixed to the case 1 non-rotatably. Thus, the boundary 28 between the body 20 of the lancet 2 is twisted and then breaks. Different from conventional arts, the user does not need to twist the cap 29, whereby the breaking of the boundary 28 is performed more easily.

As shown in FIG. 10D, the protrusion 52 enters the top end 43B" upon arriving at the second groove 43B. As already described, the top end 43B" projects beyond the top end 43A" by a predetermined distance, so that the protrusion 52 guided to the projecting end is prevented from swinging circumferentially in the housing 4. As a result, the lancet holder 5 can be held stable.

The first groove 43A of the cam mechanism C has an inclined angle θ (see FIG. 10D) which may be enlarged to reduce the force necessary to press the lancet 2 for rotating the lancet holder 5. In this state, however, the lancet 2 needs to be pressed for a longer distance until the lancet holder 5 is rotated through the desired angle. Thus, in designing the cam mechanism C, preferably the inclined angle θ is determined so that the lancet holder 5 can be rotated through an appropriate angle to twist the cap 29 off the body 20 of the lancet 2 without compromising the rotational operability of the lancet holder 5.

According to the present embodiment, the case 1 is non-rotatable relative to the housing 4 when the case 1 as a whole is externally fitted to the housing 4. However, the present invention is not limited to this. In the present invention, for example, the stopper 13 of the case 1 may pass through the groove 42 of the housing 4 after the protrusion 52 arrives at the portion shown in FIG. 10D, so that the case 1 can rotate relative to the housing 4. In this way, even if the boundary 28 between the body 20 of the lancet 2 and the cap 29 is not completely broken by rotation of the lancet holder 5, the user can rotate the case 1 to break the boundary 28.

When the case 1 is pressed upward for an appropriate distance, as shown in FIG. 12, the latch 59 is moved upward and each claw 59a is brought into engagement with the end of the cutout 44, whereby the latch 59 is latched. When the case 1 is pressed upward, as shown in FIG. 13, the side wall 31 of the sensor holder 3 is inserted into the space 60a of the holding portion 6, to receive urging force F of the spring 61. The sensor holder 3 maintains its position against the urging force F while being held by the cap 29, whereby the space 60a' is maintained between the second wall 60c and the side wall 31. The tip ends 62a of the probes 62 are pressed upward by the sensor S and come into contact with the electrodes 39b of the sensor S, while resisting the pressing force. Thus, the probes 62 and the electrodes 39b are held in reliable connection.

After completing the pressing-up step of the case 1, as shown in FIG. 14, the case 1 is removed downward from the sleeve 40a. As already described, the boundary 28 between the body 20 of the lancet 2 and the cap 29 has been broken by the twisting, whereby the lancet 2 and the cap 29 are properly divided. Due to this division, the lancet 2 is held by the lancet holder 5 with the needle 21 exposed. On the other hand, the cap 29 remains fixed to the case 1. The sensor holder 3 is detached from the cap 29 to be held by the holding portion 6.

In this way, the lancing device A enables to attach the lancet 2 to the lancet holder 5, to rotate the lancet holder 5, to twist a determined portion of the lancet 2 to be broken by the rotation of the lancet holder, and to remove the cap 29 from the body 20 by simple sliding operation of externally fitting and removing the case 1 to the sleeve 40a. As a result, comparing to conventional arts, setting of the lancet 2 is conveniently facilitated. As a user needs not to touch the lancet 2 during setting process of the lancet 2, there is no risk that the needle 21 accidentally pierces the user's finger.

The cam mechanism C is used for rotating the lancet holder 5, where the rotation of the lancet holder 5 is effectuated utilizing the pushing motion of the lancet holder 5. In this manner, no separate driving source such as a motor is needed, thereby reducing overall costs. Further, the cam mechanism C is constructed by using the housing 4 and the lancet holder 5, whereby the number of required parts is advantageously small and the increase in size can be prevented.

Additionally, in the lancing device A, the setting of the lancet 2 is performed simultaneously with the latching of the latch 59 and the setting of the sensor holder 3 to the holding portion 6. This is more convenient for the user. After detached from the body 20, the cap 29 remains fixed to the case 1. Thus, the disposal thereof is easy.

After the case 1 is removed from the sleeve 40a and the sensor holder 3 is divided from the cap 29, the side wall 31 of the sensor holder 3 is pressed against the second wall 60c by the urging force F of the spring 61. In such an instance, the sensor holder 3 is moved toward the center of the sleeve 40a (in direction of an arrow N4 in FIG. 14) by the size of the space 60a' shown in FIG. 13. Such movement of the sensor holder 3 makes the sensor S closer to the lancing portion of the lancet 2. When the sensor S is close to the lancing portion, blood from the skin reliably sticks to the sensor S on piercing the skin, as described below.

Figure 10E:
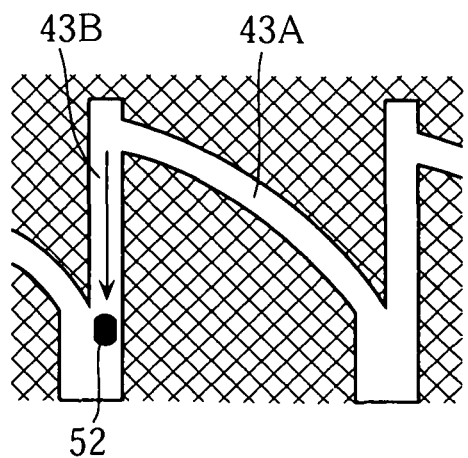
Figure 15:
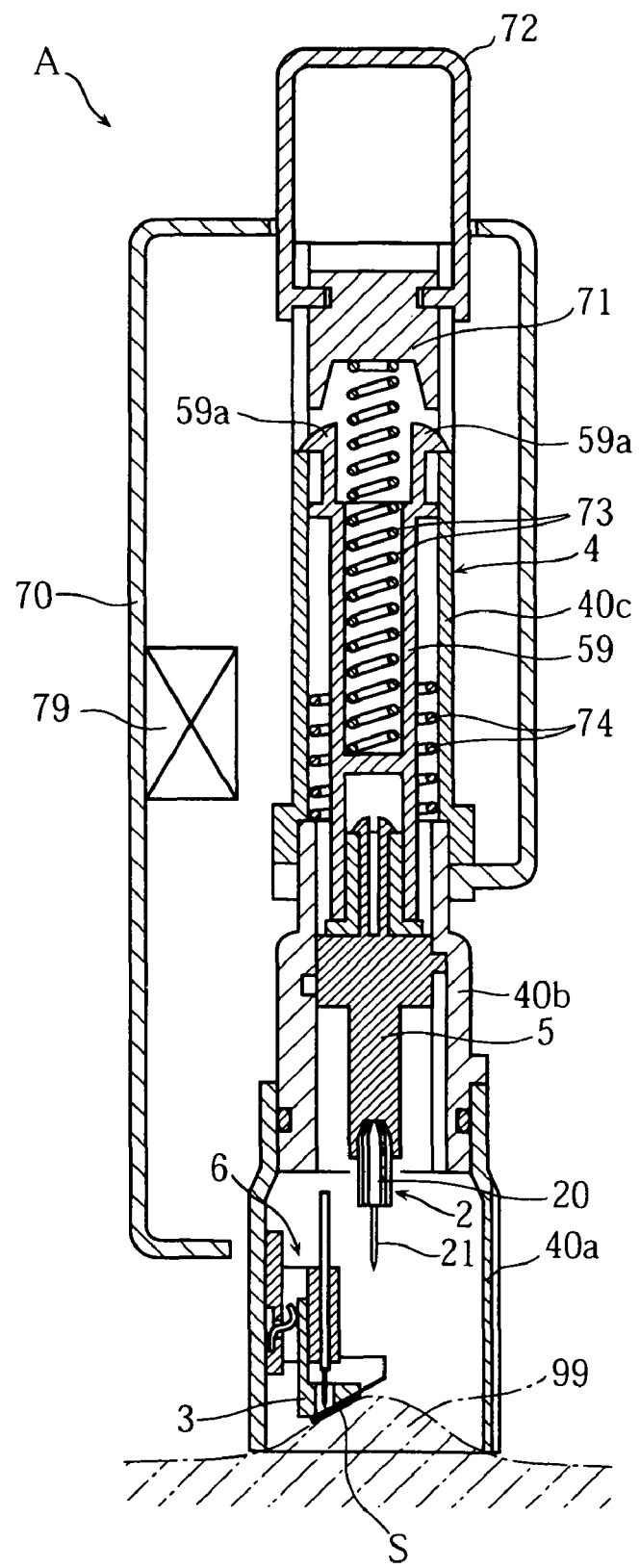
FIG. 15 is a sectional view illustrating how to use the lancing device shown in FIG. 7.

After the attaching process of the lancet 2 and the sensor 3 to the lancing device A, the tip end of the sleeve 40a of the lancing device A is pressed against human skin 99 to be lanced, as shown in FIG. 15. In this state, the operating cap 72 is pressed to advance the pusher 71. Then, as shown in FIG. 16, each claw 59a is disengaged from the end of the cutout 44, and then the latch 59 and the lancet holder 5 are moved downward by the urging force of the spring 73, whereby the needle 21 of the lancet 2 pierces the skin 99. In this step, the needle 21 can be prevented from piercing the skin 99 too deeply, by causing the body 20 of the lancet 2 partly to abut on the horizontal wall 32 of the sensor holder 3. When the lancet holder 5 is moved downward, as shown in FIG. 10E, the protrusion 52 moves within the second groove 43B, so that the lancet holder 5 advances linearly. Further, after the linear advancing, the protrusion 52 returns to the initial position shown in FIG. 1A, to be ready to repeat the operation.

Immediately after the needle 21 pierces the skin 99, the latch 59 and the lancet holder 5 are properly retracted to remove the needle 21 from the skin 99 by the urging force of the return spring 74. Preferably, the lancing device A comprises a pump or a pump mechanism for exerting negative pressure within the sleeve 40a on piercing. Due to this structure, bleeding from the skin 99 is promoted by the negative pressure so that the skin 99 is less pierced by the needle 21 of the lancet 2, and less damaged.

Blood from the skin 99 sticks to the sensor S to be introduced to the reagent 39a of the sensor S. Thereafter, the control circuit 79 calculates glucose level in the blood. The lancing device A may include a display (not shown) such as a liquid crystal display to indicate the calculated value. On the other hand, the used lancet 2 and the sensor holder 3 are removed from the lancing device A to be disposed. Such removing process utilizes a tool for inserting in the sleeve 40a to engage and hold the lancet 2 and the sensor holder 3. In this sanitary way, a user needs not to directly touch the used lancet 2 and the sensor holder 3.

The present invention is not limited to the above embodiment. Specific structure of the lancing device and the members of the cam mechanism according to the present invention may be modified in various ways. Similarly, details of each step in the method of setting the lancing member in the lancing device according to the present invention may be also modified in various ways.

Figure 17:
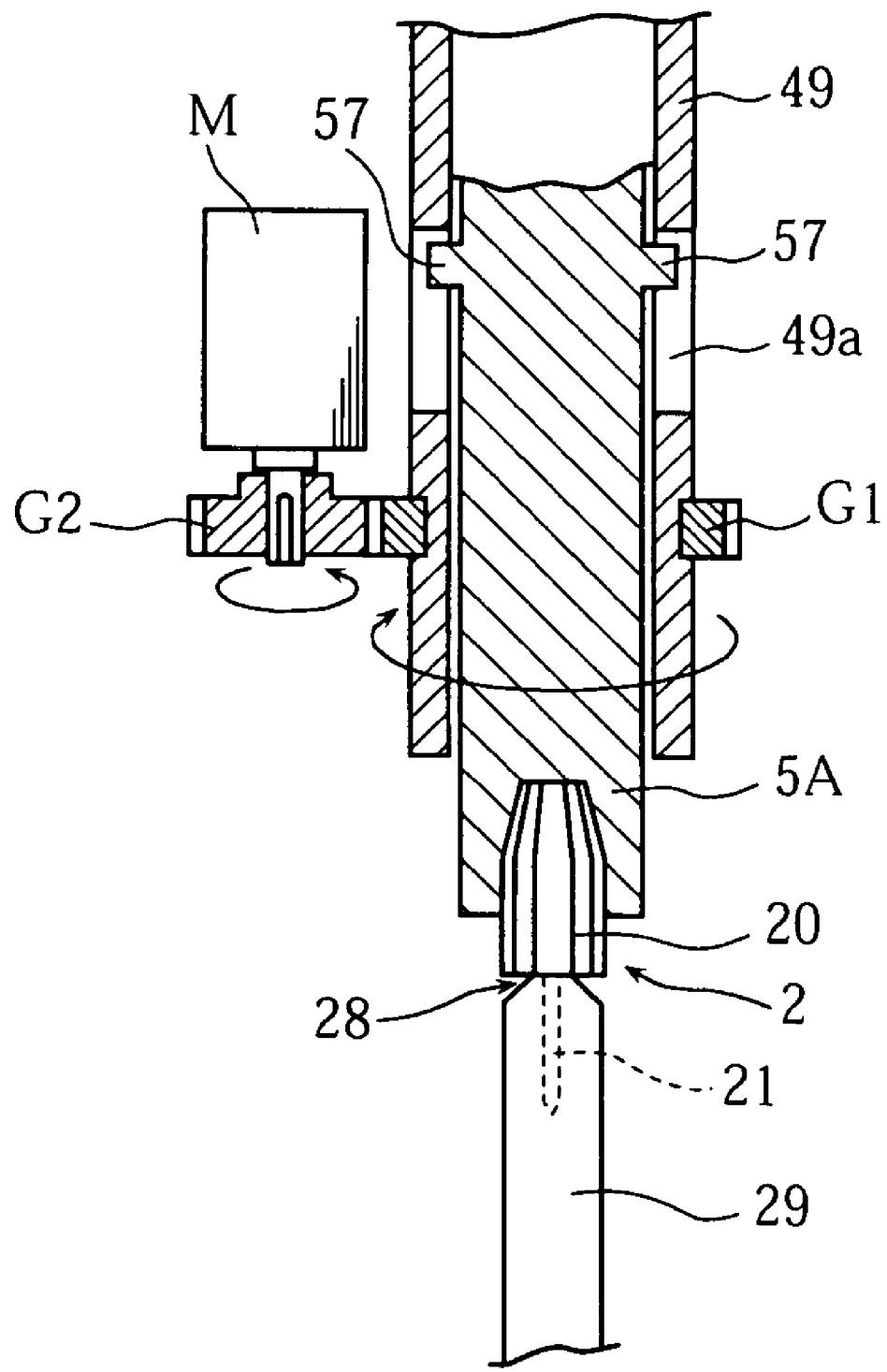
FIG. 17 is an enlarged sectional view illustrating another example of a lancing device according to the present invention.
Figure 18A:
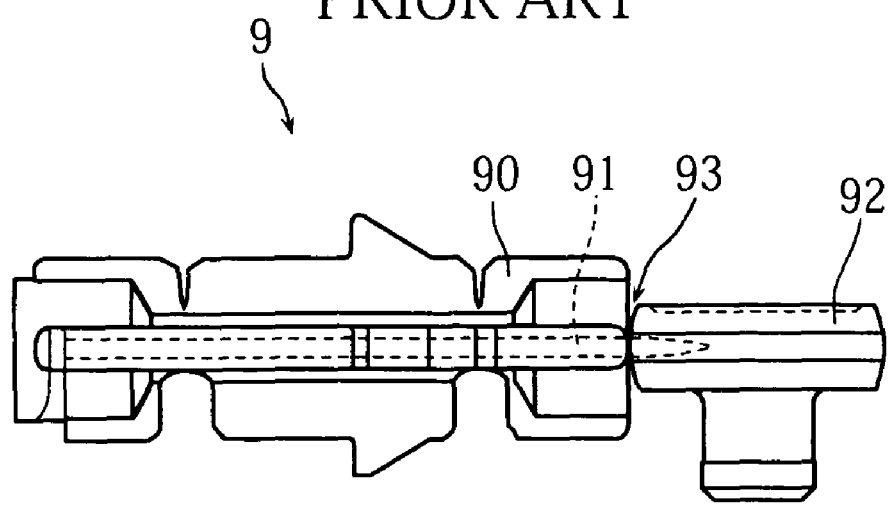
FIGS. 18A-18B are side views illustrating prior art.
Figure 18B:
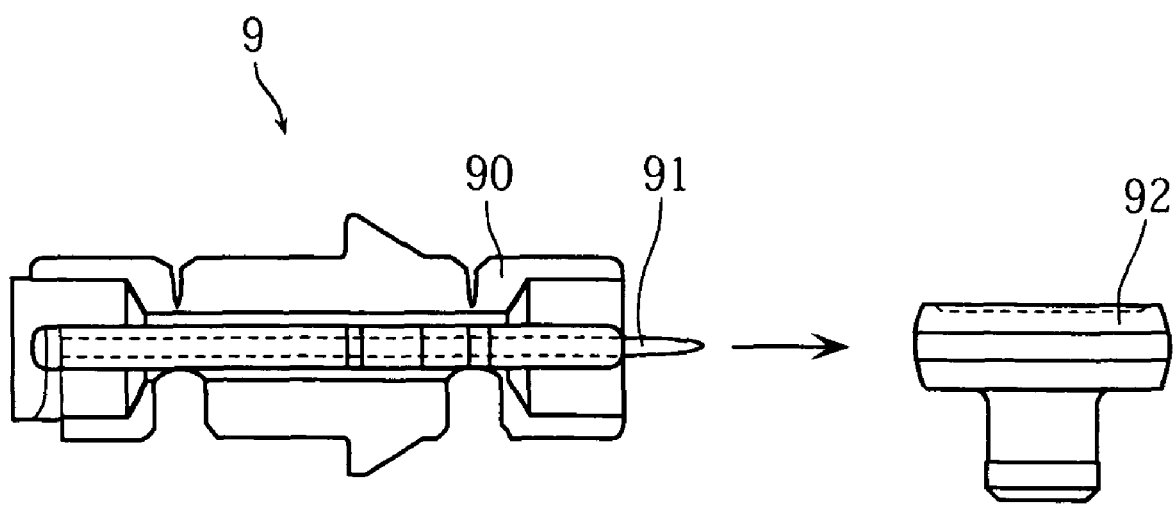

The lancing member may be rotated by various means in place of the cam mechanism. FIG. 17 illustrates another example of a lancing device according to the present invention. The illustrated lancing device includes a housing having a sleeve 49 for reciprocally holding a lancet holder 5A, and a gear G1 externally fixed to the circumference of the sleeve 49. The gear G1 is engaged with a gear G2 fixed to a drive shaft of a motor M. The lancet holder 5A is externally formed with a pair of protrusions 57. The protrusions 57 are engaged with a pair of slots 49a formed at the sleeve 49. In the lancing device, the motor M is driven to rotate the gear G2, then the gear G1 rotates together with the sleeve 49, thereby rotating the lancet 5A. Thus, with the lancet 2 held by the lancet holder 5, it is possible to twist off the boundary 28 between the body 20 and the cap 29 by causing the motor M to rotate the lancet 2.

As described above, according to the present invention, the lancing device may be provided with a motor for rotating a holder and a lancing member. The motor may be operated by a user using a predetermined switch, for example. However, for improving user's convenience, preferably, the motor may be automatically switched on to be driven when the lancing member is attached to the holder of the lancing device, so that the user needs not to operate a switch.

According to the present invention, a lancing member and a holder may be rotated during attaching process of the lancing member to the holder, instead of being rotated after the lancing member is held by the holder. For instance, in attaching the lancing member to the holder, the holder may be rotated before the attachment has been completed, and the lancing member and the holder are rotated together.

According to the present invention, the lancing member is not necessarily formed integral with the cap. Instead, the lancing member may be formed separate from the cap, and the cap may be attached to the lancing member by an adhesive. In the cam mechanism, it is not necessarily required that the movable member is formed with protrusions and the housing formed with guiding grooves. On the contrary, the movable member may be formed with grooves, and the housing may be formed with protrusions.

The holder of a lancing device is not limited to the one in which the lancing member is held by fitting insertion. For instance, the lancing member may be held by a clamping mechanism. The mechanism for advancing the holder may various in design other than the one utilizing the restoring force of a spring.

A lancing device according to the present invention is not limited to be used for measuring the glucose level in blood. Further, a lancing device according to the present invention may be used without attaching an analyzer such as a sensor holder.

The invention claimed is:

1. A cam mechanism for rotating a lancet relative to a cap, the lancet including a body and a lancing needle projecting from the body, the cap being initially integral with the body of the lancet and subsequently removable from the body by rotating the cap relative to the lancet, the cam mechanism comprising:
 a cylindrical housing separate from the cap;
 a movable member contained in the housing for moving reciprocally in first and second directions parallel to a longitudinal axis of the housing, the movable member holding the lancet and configured to allow the lancet to rotate relative to the cap that covers the lancing element of the lancet;
 a first groove inclined relative to the axis of the housing and a second groove connected to the first groove and extending linearly in parallel to the axis of the housing, the first and the second grooves being provided at one of the housing and the movable member; and
 a protrusion provided at the other one of the housing and the movable member, the protrusion extending into the first groove and the second groove;

wherein the protrusion moves in the first groove when the movable member moves in the first direction, and moves in the second groove when the movable member moves in the second direction.

2. A lancing device comprising:

a cylindrical housing;

a lancet holder that holds a lancet including a body and a lancing needle projecting from the body, the lancing needle being covered by a cap that is separate from the housing and initially integral with the body of the lancet, the lancet holder being reciprocally movable along a longitudinal axis of the housing;

a moving mechanism for advancing the lancet holder along the longitudinal axis of the housing; and a cam mechanism for converting a retracting movement of the lancet holder along the longitudinal axis of the housing into rotation of the lancet holder and the lancet relative to the cap for removing the cap from the body of the lancet.

3. The lancing device according to claim 2, wherein the lancet holder holds the lancet in a manner such that the lancet holder and the lancet are not rotatable relative to each other, wherein the cam mechanism causes the lancet holder to rotate together with the lancet.

4. The lancing device according to claim 2, wherein the cam mechanism includes a first groove which is provided on the housing and is inclined relative to the longitudinal axis of the housing, and a protrusion which is provided on the lancet holder and is fitted in the first groove.

5. The lancing device according to claim 4, wherein the cam mechanism further includes a second groove connected to the first groove and extending in parallel to the longitudinal axis of the housing, and wherein the protrusion passes through the second groove when the lancet holder advances.

6. The lancing device according to claim 2, further comprising a holding portion for removably holding an analyzer used for analyzing a sample taken by a piercing process.

7. The lancing device according to claim 6, further comprising a control circuit for analyzing the sample using the analyzer.

* * * * *